US012096952B2

United States Patent
Pham et al.

(10) Patent No.: US 12,096,952 B2
(45) Date of Patent: Sep. 24, 2024

(54) FORCEPS BLADE GUIDE

(71) Applicant: GYRUS ACMI, INC., Southborough, MA (US)

(72) Inventors: Hanam Pham, Minneapolis, MN (US); Zane R. Ward, Minneapolis, MN (US); John Mensch, Plymouth, MN (US); Jeffrey D. Holton, Stanchfield, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 1012 days.

(21) Appl. No.: 16/830,201

(22) Filed: Mar. 25, 2020

(65) Prior Publication Data
US 2020/0305965 A1    Oct. 1, 2020

Related U.S. Application Data

(60) Provisional application No. 62/994,220, filed on Mar. 24, 2020, provisional application No. 62/841,476, (Continued)

(51) Int. Cl.
*A61B 17/28* (2006.01)
*A61B 17/128* (2006.01)
(Continued)

(52) U.S. Cl.
CPC ........ *A61B 17/282* (2013.01); *A61B 17/1285* (2013.01); *A61B 17/2804* (2013.01); *A61B 17/2833* (2013.01); *A61B 17/285* (2013.01); *A61B 17/2909* (2013.01); *A61B 18/1445* (2013.01); *A61B 18/149* (2013.01);
(Continued)

(58) Field of Classification Search
CPC ................. A61B 17/29; A61B 17/295; A61B 2017/2926; A61B 2017/2932; A61B 2017/2933; A61B 18/1442; A61B 18/1445; A61B 2018/1452; A61B 2018/1455
See application file for complete search history.

(56) References Cited

U.S. PATENT DOCUMENTS 4,887,612 A    12/1989    Esser et al.
6,458,130 B1   10/2002    Frazier et al.
(Continued)

FOREIGN PATENT DOCUMENTS

WO    WO-2009070780 A1    6/2009

OTHER PUBLICATIONS

"U.S. Appl. No. 16/830,150, Advisory Action mailed May 18, 2022", 3 pgs.
(Continued)

*Primary Examiner* — Daniel W Fowler
*Assistant Examiner* — Bradford C. Blaise
(74) *Attorney, Agent, or Firm* — Schwegman Lundberg Woessner, P.A.

(57) ABSTRACT

Surgical forceps can include a jaw, a blade, and a tongue. The jaw can include a grip surface defining a slot. The blade can be configured to reciprocate along the slot between an extended position and a retracted position. The tongue can be connected to the jaw where at least a portion of the tongue can be located proximal of the grip surface to guide the blade into the blade slot when the blade moves from the retracted position into the blade slot.

16 Claims, 10 Drawing Sheets

Related U.S. Application Data filed on May 1, 2019, provisional application No. 62/826,522, filed on Mar. 29, 2019, provisional application No. 62/826,532, filed on Mar. 29, 2019.

(51) Int. Cl.
| | |
|---|---|
| A61B 17/285 | (2006.01) |
| A61B 17/29 | (2006.01) |
| A61B 17/295 | (2006.01) |
| A61B 17/32 | (2006.01) |
| A61B 18/00 | (2006.01) |
| A61B 18/14 | (2006.01) |
| A61B 90/00 | (2016.01) |
| B23K 26/21 | (2014.01) |

(52) U.S. Cl.
CPC ............ *A61B 90/03* (2016.02); *B23K 26/21* (2015.10); *A61B 2017/2845* (2013.01); *A61B 17/29* (2013.01); *A61B 2017/2901* (2013.01); *A61B 2017/2902* (2013.01); *A61B 2017/2903* (2013.01); *A61B 2017/2908* (2013.01); *A61B 2017/2912* (2013.01); *A61B 2017/2916* (2013.01); *A61B 2017/2917* (2013.01); *A61B 2017/2919* (2013.01); *A61B 2017/292* (2013.01); *A61B 2017/2925* (2013.01); *A61B 2017/2926* (2013.01); *A61B 2017/2933* (2013.01); *A61B 2017/2936* (2013.01); *A61B 2017/2945* (2013.01); *A61B 2017/2946* (2013.01); *A61B 2017/2947* (2013.01); *A61B 2017/2948* (2013.01); *A61B 17/295* (2013.01); *A61B 2017/320052* (2013.01); *A61B 2017/320095* (2017.08); *A61B 2018/00148* (2013.01); *A61B 2018/00196* (2013.01); *A61B 2018/00202* (2013.01); *A61B 2018/00309* (2013.01); *A61B 2018/00345* (2013.01); *A61B 2018/00601* (2013.01); *A61B 2018/0063* (2013.01); *A61B 2018/00636* (2013.01); *A61B 2018/0091* (2013.01); *A61B 2018/00916* (2013.01); *A61B 2018/00946* (2013.01); *A61B 2018/00952* (2013.01); *A61B 2018/1412* (2013.01); *A61B 18/1442* (2013.01); *A61B 18/1447* (2013.01); *A61B 2018/1455* (2013.01); *A61B 2018/1457* (2013.01); *A61B 2090/034* (2016.02)

(56) References Cited

U.S. PATENT DOCUMENTS

| | | |
|---|---|---|
| 7,131,971 B2 | 11/2006 | Pycus et al. |
| 8,540,711 B2 | 9/2013 | Dycus et al. |
| 8,663,270 B2 | 3/2014 | Donnigan et al. |
| 8,715,277 B2 | 5/2014 | Weizman |
| 8,968,311 B2 | 3/2015 | Allen, IV et al. |
| 8,968,313 B2 | 3/2015 | Larson |
| 9,636,169 B2 | 5/2017 | Allen, Iv et al. |
| 9,681,883 B2 | 6/2017 | Windgassen et al. |
| 9,820,765 B2 | 11/2017 | Allen, Iv et al. |
| 10,485,566 B2 | 11/2019 | Nelson et al. |
| 10,722,317 B2 | 7/2020 | Ward et al. |
| 11,911,058 B2 | 2/2024 | Pham et al. |
| 2003/0018331 A1 | 1/2003 | Dycus et al. |
| 2005/0119655 A1 | 6/2005 | Moses et al. |
| 2006/0189981 A1 | 8/2006 | Dycus et al. |
| 2010/0010512 A1 | 1/2010 | Taylor et al. |
| 2010/0057085 A1 | 3/2010 | Holcomb et al. |
| 2010/0274244 A1 | 10/2010 | Heard |
| 2011/0184405 A1 | 7/2011 | Mueller |
| 2013/0014375 A1 | 1/2013 | Hempstead et al. |
| 2013/0218198 A1 | 8/2013 | Larson et al. |
| 2013/0296848 A1 | 11/2013 | Allen, Iv et al. |
| 2013/0304058 A1 | 11/2013 | Kendrick |
| 2013/0345702 A1* | 12/2013 | Wandel ............... A61B 18/1445 606/45 |
| 2014/0025071 A1 | 1/2014 | Sims et al. |
| 2015/0133931 A1 | 5/2015 | Twomey et al. |
| 2015/0150573 A1 | 6/2015 | Van Tol et al. |
| 2015/0209103 A1* | 7/2015 | Artale ................ A61B 18/1206 606/42 |
| 2016/0015419 A1 | 1/2016 | Hibner et al. |
| 2017/0128071 A1 | 5/2017 | Holsten et al. |
| 2017/0196648 A1 | 7/2017 | Ward et al. |
| 2017/0238990 A1* | 8/2017 | Soni .................. A61B 18/1445 |
| 2018/0161112 A1* | 6/2018 | Weir ..................... A61B 34/00 |
| 2018/0338792 A1 | 11/2018 | Allen, Iv et al. |
| 2019/0175256 A1 | 6/2019 | Butler |
| 2019/0298399 A1 | 10/2019 | Boone et al. |
| 2020/0163687 A1 | 5/2020 | Ding et al. |
| 2020/0281683 A1 | 9/2020 | Ward et al. |
| 2020/0305911 A1 | 10/2020 | Pham et al. |
| 2021/0346044 A1 | 11/2021 | Fiksen et al. |

OTHER PUBLICATIONS

"U.S. Appl. No. 16/830,150, Non Final Office Action mailed Sep. 7, 2022", 20 pgs.

"U.S. Appl. No. 16/830,150, Response filed May 5, 2022 to Final Office Action mailed Mar. 30, 2022", 14 pgs.

"U.S. Appl. No. 16/830,150, Response filed Jun. 21, 2022 to Advisory Action mailed May 18, 2022", 16 pgs.

"U.S. Appl. No. 16/830,150, Examiner Interview Summary mailed Oct. 17, 2022", 2 pgs.

"U.S. Appl. No. 16/830,150, Response filed Oct. 12, 2022 to Non Final Office Action mailed Sep. 7, 2022", 13 pgs.

U.S. Appl. No. 16/830,150, filed Mar. 25, 2020, Forceps Drive Shaft.

U.S. Appl. No. 15/403,515, 10,722,317, filed Jan. 11, 2017, Forceps With Tissue Stops.

U.S. Appl. No. 16/884,382, filed May 27, 2020, Forceps With Tissue Stops.

"U.S. Appl. No. 15/403,515, Corrected Notice of Allowability mailed May 12, 2020", 2 pgs.

"U.S. Appl. No. 16/830,150, Examiner Interview Summary mailed Dec. 10, 2021", 3 pgs.

"U.S. Appl. No. 16/830,150, Final Office Action mailed Mar. 30, 2022", 19 pgs.

"Application Serial No. 16/830, 150, Non Final Office Action mailed Oct. 29, 21", 15 pgs.

"U.S. Appl. No. 16/830,150, Response filed Dec. 10, 2021 to Non Final Office Action mailed Oct. 29, 2021", 13 pgs.

"U.S. Appl. No. 16/830,150, Final Office Action mailed May 3, 2023", 25 pgs.

"U.S. Appl. No. 16/830,150, Non Final Office Action mailed Jan. 18, 2023", 24 pgs.

"U.S. Appl. No. 16/830,150, Response filed Feb. 10, 2023 to Non Final Office Action mailed Jan. 18, 2023", 13 pgs.

"U.S. Appl. No. 16/830,150, Notice of Allowance mailed Aug. 16, 2023", 18 pgs.

"U.S. Appl. No. 16/830,150, Notice of Allowance mailed Sep. 22, 2023", 7 pgs.

"U.S. Appl. No. 16/830,150, Response filed Jun. 26, 2023 to Final Office Action mailed May 3, 2023", 15 pgs.

"U.S. Appl. No. 16/884,382, Non Final Office Action mailed Jun. 23, 2023", 12 pgs.

"U.S. Appl. No. 16/884,382, Response filed Sep. 21, 2023 to Non Final Office Action mailed Jun. 23, 2023", 14 pgs.

"U.S. Appl. No. 16/830,150, Corrected Notice of Allowability mailed Jan. 11, 2024", 2 pgs.

"U.S. Appl. No. 16/884,382, Final Office Action mailed Dec. 19, 2023", 7 pgs.

"U.S. Appl. No. 16/884,382, Notice of Allowance mailed Feb. 20, 2024", 5 pgs.

(56) References Cited

OTHER PUBLICATIONS

"U.S. Appl. No. 16/884,382, Response filed Jan. 24, 2024 to Final Office Action mailed Dec. 19, 2023", 7 pgs.

* cited by examiner

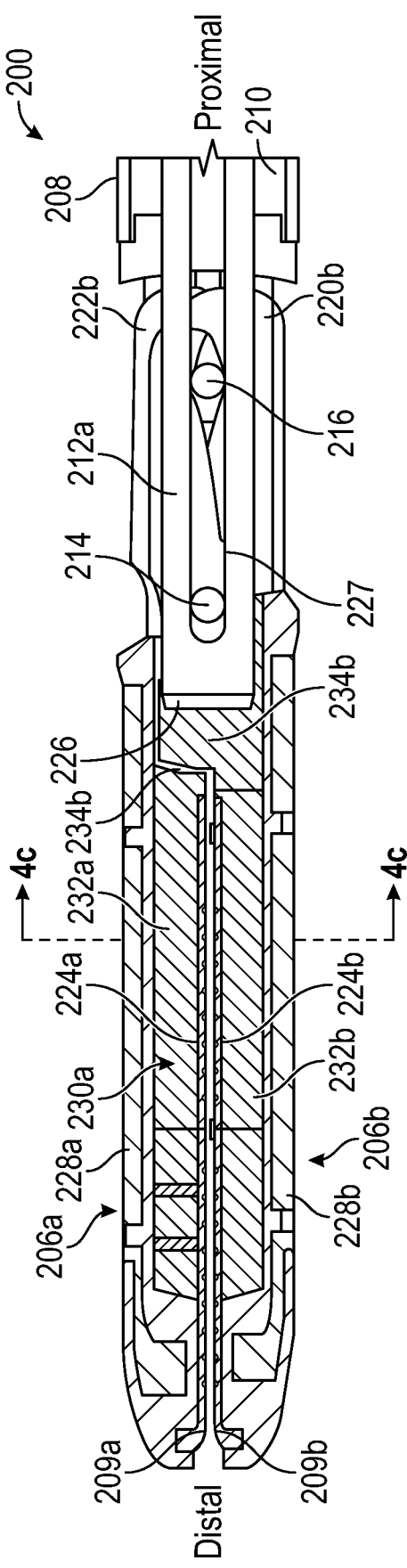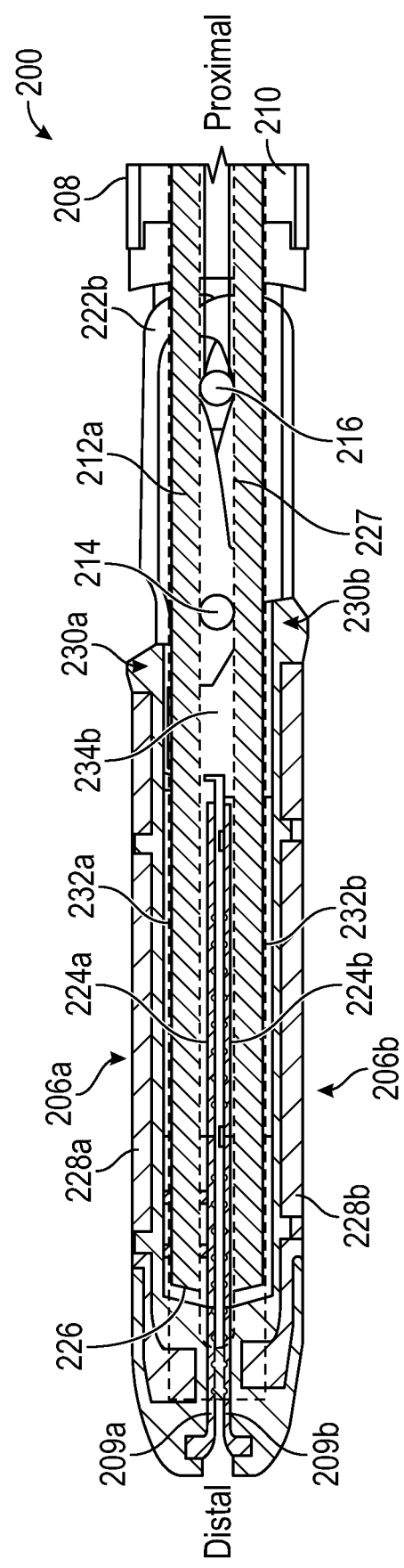

FORCEPS BLADE GUIDE

CLAIM OF PRIORITY

This patent application claims the benefit of priority, under 35 U.S.C. Section 119(e), to U.S. Ser. No. 62/826,532, filed on Mar. 29, 2019, entitled "BLADE ASSEMBLY FOR FORCEPS", and to U.S. Ser. No. 62/826,522 filed on Mar. 29, 2019, entitled "SLIDER ASSEMBLY FOR FORCEPS", the disclosure of which is incorporated by reference in its entirety, and to U.S. Ser. No. 62/841,476, filed on May 1, 2019, entitled "FORCEPS WITH CAMMING JAWS", and to U.S. Ser. No. 62/994,220, filed on Mar. 24, 2020, entitled "FORCEPS DEVICES AND METHODS" each of which is hereby incorporated by reference herein in its entirety.

BACKGROUND

Medical devices for diagnosis and treatment, such as forceps, are often used for medical procedures such as laparoscopic and open surgeries. Forceps can be used to manipulate, engage, grasp, or otherwise affect an anatomical feature, such as a vessel or other tissue of a patient during the procedure. Forceps often include an end effector that is manipulatable from a handle of the forceps. For example, jaws located at a distal end of a forceps can be actuated via elements of the handle between open and closed positions to thereby engage the vessel or other tissue. Forceps can include an extendable and retractable blade that can be extended distally between a pair of jaws to lacerate the tissue. The handle can also be capable of supplying an input energy, such as electromagnetic energy or ultrasound, to the end effector for sealing of the vessel or tissue during the procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3B illustrates a side cross-sectional view of forceps in a closed position with a blade retracted.

FIG. 3C illustrates a side cross-sectional view of forceps in a closed position with a blade extended.

DETAILED DESCRIPTION

Electrosurgical forceps often include a blade for cutting tissue. The blade can be positioned within a shaft of the forceps and can be operated from a handle of the forceps to extend between jaws of the forceps to cut tissue between the jaws. During use, the blade can be translated between a fully retracted (proximal) position and a fully extended (distal position). The blade must often be guided when moving from the retracted position to the extended position to avoid or limit contact between a distal (sharpened) tip or edge of the blade and components of the jaw. Such contact can damage or otherwise cause the blade to dull, which can reduce cutting effectiveness of the blade and therefore of the forceps. Blade guides exist for controlling distal extension of the blade; however, such blade stops often require one or more additional components to act as a blade guide. Such components can increase product complexity and ultimately product cost.

The present disclosure can help to address these issues by using tongues or tissue stops of the jaws to guide distal translation of the blade. In this way, a component used for limiting tissue movement between the jaws can additionally be used to guide extension of the blade into blade tracks of the jaws during operation, which can help reduce a total number of components of the forceps, helping to save cost.

The above discussion is intended to provide an overview of subject matter of the present patent application. It is not intended to provide an exclusive or exhaustive explanation of the invention. The description below is included to provide further information about the present patent application.

Figure 1:
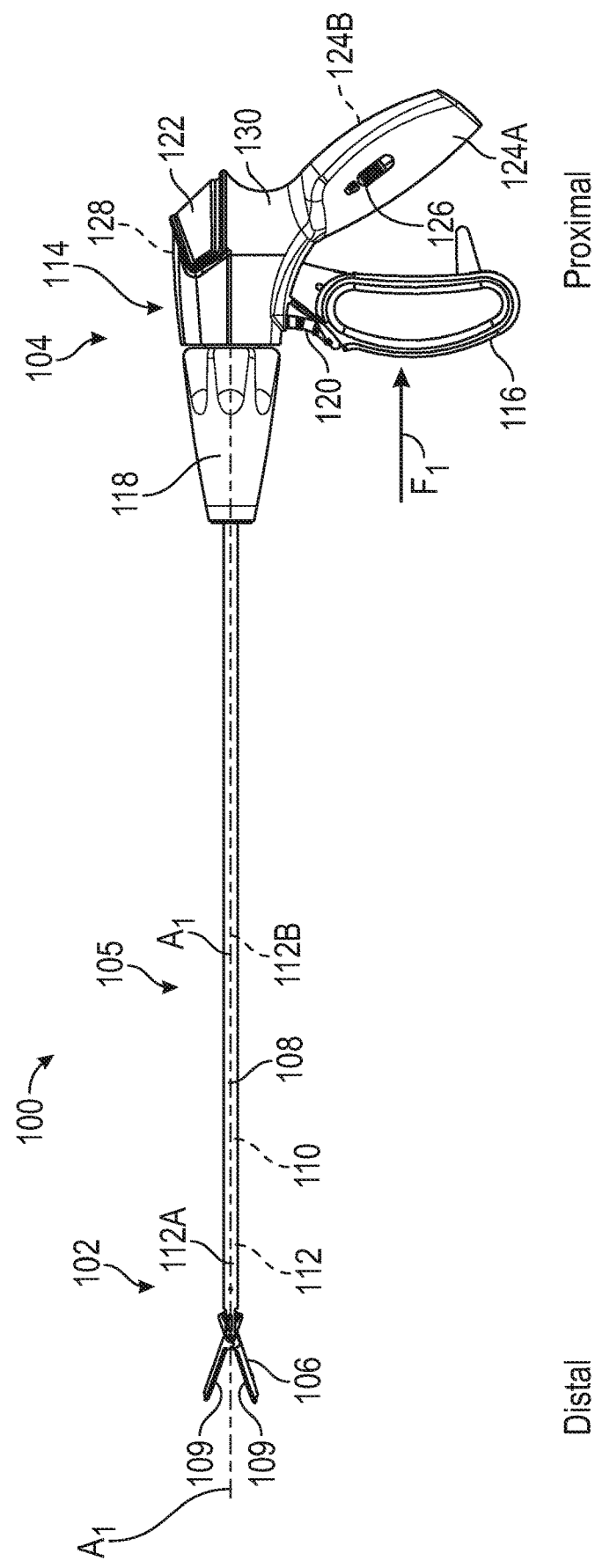
FIG. 1 illustrates a side view of a forceps showing jaws in an open position.

FIG. 1 illustrates a side view of a forceps 100 showing jaws in an open position. The forceps 100 can include an end effector 102, a handpiece 104, and an intermediate portion 105. The end effector 102 can include jaws 106 (including electrodes 109), an outer shaft 108, an inner shaft 110, and a blade assembly 112. The handpiece 104 can include a housing 114, a lever 116, a rotational actuator 118, a trigger 120, an activation button 122, a fixed handle 124a and 124b, and a handle locking mechanism 126. The housing 114 can include a first housing portion 128, and a second housing portion 130. FIG. 1 also shows orientation indicators Proximal and Distal and a longitudinal axis A1.

Generally, the handpiece 104 can be located at a proximal end of the forceps 100 and the end effector 102 can be located at the distal end of the forceps 100. The intermediate portion 105 can extend between the handpiece 104 and the end effector 102 to operably couple the handpiece 104 to the end effector 102. Various movements of the end effector 102 can be controlled by one or more actuation systems of the handpiece 104. For example, the end effector 102 can be rotated along the longitudinal axis A1 of the forceps 100. Also, the handpiece can operate the jaws 106, such as by moving the jaws 106 between open and closed position. The handpiece 104 can also be used to operate the blade assembly 112 for cutting tissue and can operate the electrode 109 for applying electromagnetic energy to tissue. The end effector 102, or a portion of the end effector 102, can be one or more of: opened, closed, rotated, extended, retracted, and electromagnetically energized.

The housing 114 can be a frame that provides structural support between components of the forceps 100. The housing 114 is shown as housing at least a portion of the actuation systems associated with the handpiece 104 for actuating the end effector 102. However, some or all of the actuation components need not be housed within the housing 114 The housing 114 can provide a rigid structure for attachment of components, but the housing 114 does not necessarily house the components completely, or can house a portion of one or more of the components.

The drive shaft 110 can extend through the housing 114 and out of a distal end of the housing 114, or distally beyond housing 114. The jaws 106 can be connected to a distal end of the drive shaft 110. The outer shaft 108 can be a hollow tube positioned around the drive shaft 110. A distal end of the outer shaft 108 can be located adjacent the jaws 106. The distal ends of the drive shaft 110 and the outer shaft 108 can be rotationally locked to the jaws 106. The rotational actuator 118 can be positioned around the distal end of the housing 114. The outer shaft 108 can extend distally beyond the rotational actuator 118. The blade shaft 112b can extend through the drive shaft 110 and the outer shaft 108. A distal end of the blade shaft 112b can be located near the jaws 106. A proximal end of the blade shaft 112b can be within housing 114.

The handpiece 104 can enable a user to extend and retract a blade 112a of the blade assembly 112, which can be attached to a distal end of a blade shaft 112b of the blade assembly 112. In some examples, the blade 112a can extend an entirety of a length between the handle 104 and the end effector 102. In some examples, the handpiece 104 can include features that inhibits the blade assembly 112 from being extended until the jaws 106 are at least partially closed, or fully closed. The blade 112a can be extended by displacing the trigger 120 proximally and the blade 112a can be retracted by allowing the trigger 120 to return distally to a default position.

A proximal portion of the trigger 120 can be connected to the blade shaft 112b within the housing 114 and a distal portion of the trigger 120 can extend outside of the housing 114 adjacent to, and in some examples nested with, the lever 116 in the default or unactuated positions. The activation button 122 can be coupled to the housing 114 and can include or be connected to electronic circuitry within the housing 114. Such circuitry can send or transmit electromagnetic energy through forceps 100 to the jaws 106. In some examples, the electronic circuitry may reside outside the housing 114 but can be operably coupled to the housing 114 and the end effector 102.

In operation of the end effector 100, a user can displace the lever 116 proximally by applying a Force FI to the lever 116 to actuate the drive shaft 110 to drive the jaws 106 from the open position (FIG. 2C) to the closed position (FIG. 2A), which can allow the user to clamp down on and compress a tissue. The handpiece 104 can also allow a user to rotate the rotational actuator 118 to cause the end effector 102 to rotate, such as by rotating both the drive shaft 110 and the outer shaft 108 together.

In some examples, with the tissue compressed, a user can depress the activation button 122 to cause an electromagnetic energy, or in some examples, ultrasound, to be delivered to the end effector 102, such as to the electrode 109 and to the tissue. Application of such energy can be used to seal or otherwise affect the tissue being clamped. In some examples, the electromagnetic energy can cause tissue to be coagulated, sealed, ablated, or can cause controlled necrosis. When desired, the trigger 120 can be moved to translate the blade assembly 112 distally such that the blade 112a can extend between the jaws 106 in order to cut the tissue within the jaws 106. Such a process can be repeated, as desired.

In some examples, the forceps 100, or other medical device, may not include all the features described or may include additional features and functions, and the operations may be performed in any order. The handpiece 104 can be used with a variety of other end effectors to perform other methods.

Figure 2A:
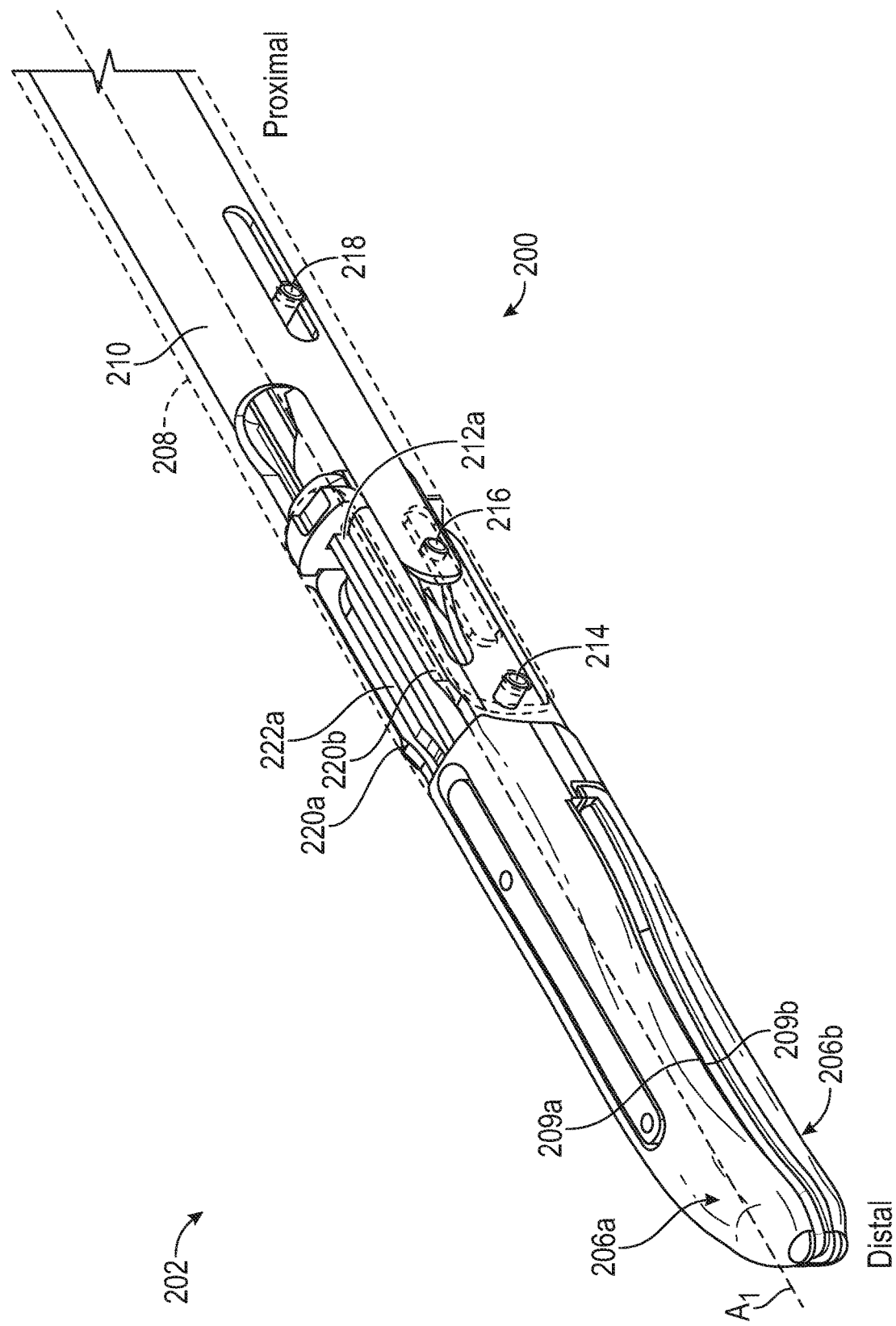
FIG. 2A illustrates an isometric view of a portion of forceps in a closed position.
Figure 2B:
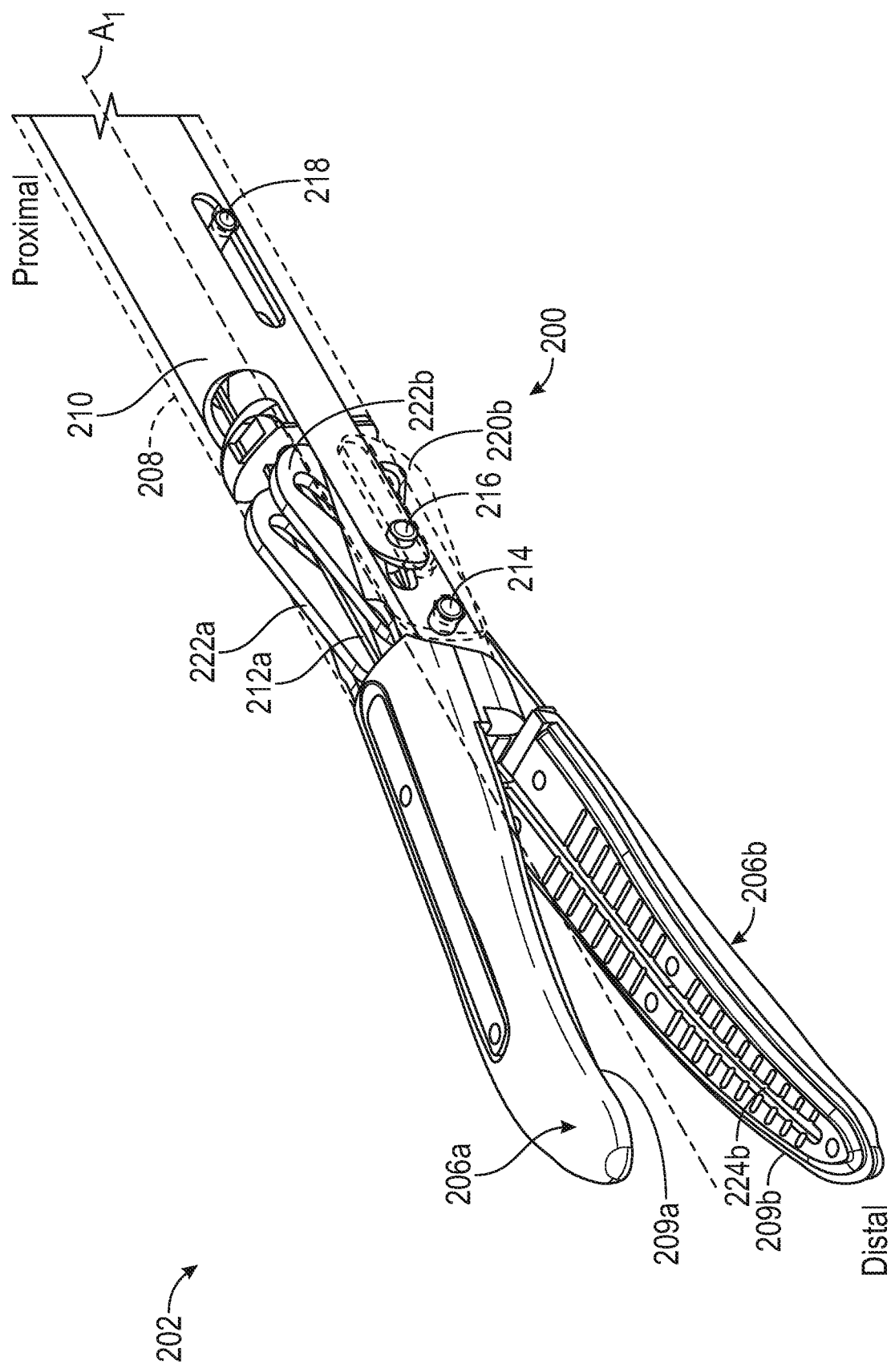
FIG. 2B illustrates an isometric view of a portion of forceps in a partially open position.
Figure 2C:
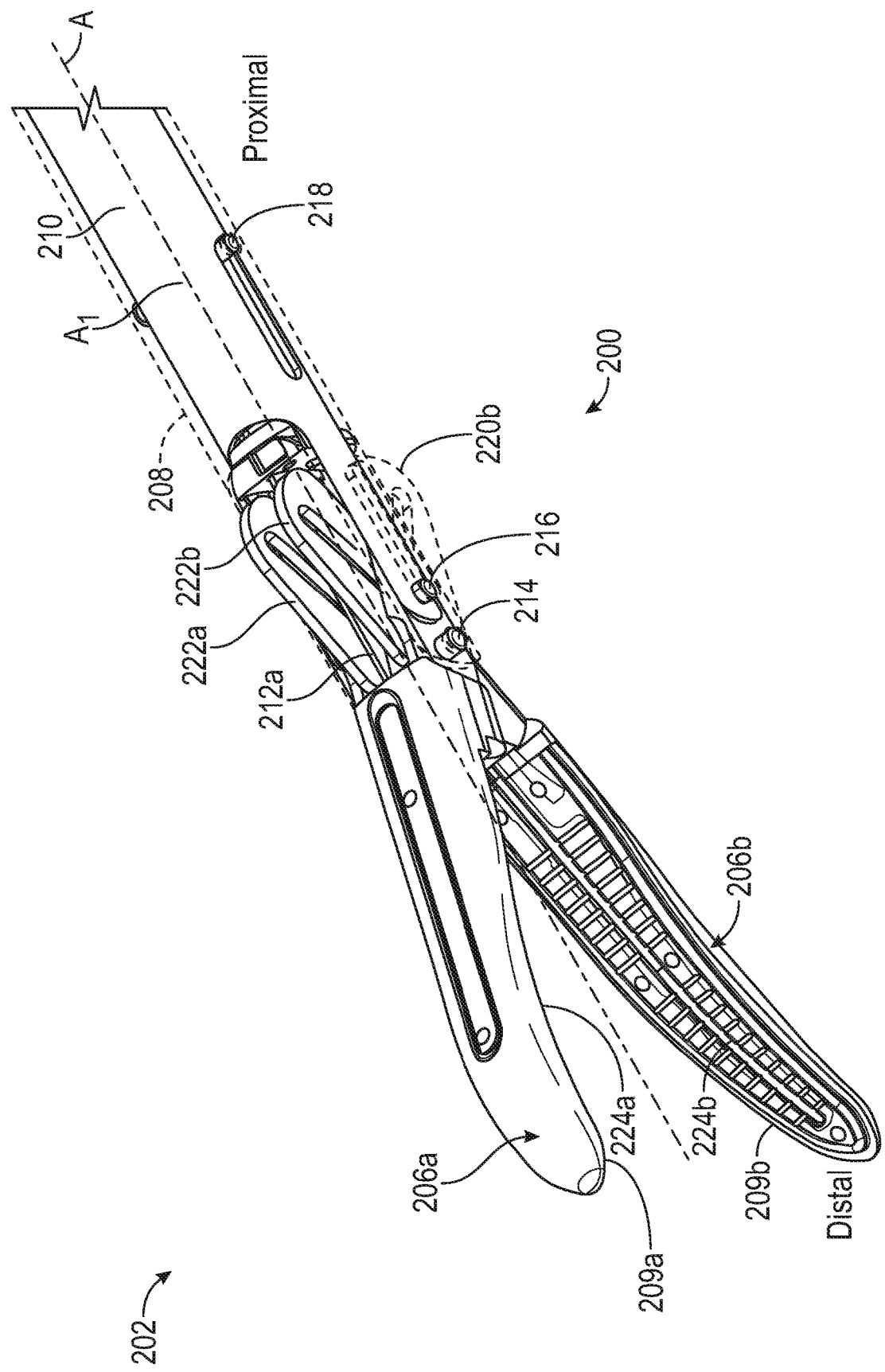
FIG. 2C illustrates an isometric view of a portion of forceps in an open position.

FIG. 2A illustrates an isometric view of a portion of forceps 200 in a closed position. FIG. 2B illustrates an isometric view of a portion of the forceps 200 in a partially open position. FIG. 2C illustrates an isometric view of a portion of the forceps 200 in an open position. FIGS. 2A-2C are discussed below concurrently.

The forceps 200 can include an end effector 202 that can be connected to a handle (such as the handle 104). The end effector 202 can include jaws 206a and 206b, an outer shaft 208, grip plates 209a and 209b, an inner shaft 210, a blade assembly 212, a pivot pin 214, a drive pin 216, and a guide pin 218. The jaw 206a can include flanges 220a and 220b, and the jaw 206b can include flanges 222a and 222b. The grip plate 209a can include a blade slot 224a and the grip plate 209b can include a blade slot 224b. The blade assembly 212 can include a blade 212a and a shaft 212b. FIGS. 2A-2C also show orientation indicators Proximal and Distal and a longitudinal axis A1.

Any of the components of the forceps 200 can be comprised of materials such as one or more of metals, plastics, foams, elastomers, ceramics, composites, combinations thereof, or the like. Materials of some components of the forceps 200 are discussed below in further detail.

The jaws 206a and 206b (collectively referred to as jaws 206) can be rigid or semi-rigid members configured to engage tissue. The jaws 206a and 206b can be coupled to the outer shaft 208, such as pivotably coupled, via the pivot pin 214. The pivot pin 214 can extend through a portion of the jaws 206a and 206b (such as a bore of each of the jaws 206a and 206b) such that the pivot pin 214 can be received by outer arms of the outer shaft 208. In other examples, the jaws 206a and 206b can be pivotably coupled to the outer shaft 208 via a boss or bosses of the outer shaft 208. In another example, the jaws 206a and 206b can include a boss (or bosses) receivable in bores of the outer shaft 208 to pivotably couple the jaws 206a and 206b to the outer shaft 208. In another example, outer shaft 208 can include a boss (or bosses) receivable in bores of the jaws 206a and 206b to pivotably couple the jaws 206a and 206b to the outer shaft 208.

The flanges 220a and 220b (which can be a set of flanges, that is, two flanges) can be rigid or semi-rigid members located at a proximal portion of the jaw 206a. Similarly, the flanges 222a and 222b can be rigid or semi-rigid members located at a proximal portion of the jaw 206b. In some examples, the flanges 220 can be positioned laterally outward of the inner flanges 222. In other examples, the flanges 220 and 222 can be interlaced.

The grip plates 209a and 209b of the jaws 206a and 206b can each be a rigid or semi-rigid member configured to engage tissue and/or the opposing jaw to grasp tissue, such as during an electrosurgical procedure. One or more of the grip plates 209a and 209b can include one or more of serrations, projections, ridges, or the like configured to increase engagement pressure and friction between the grip plates 209a and 209b and tissue. The flanges 220 of the upper jaw 206a can extend proximally away from the grip plate 209a and 209b, and in some examples, substantially downward when the upper jaw 206a is in the open and partially open positions (as shown in FIGS. 2B and 2C, respectively). Similarly, the flanges 222 of the lower jaw 206b can extend proximally away from the grip plate, and in some examples, substantially upward when the upper jaw 206a is in the open and partially open positions (as shown in FIGS. 2B and 2C, respectively), such that the jaws 206a and 206b and flanges 220 and 222 operate to open and close in a scissoring manner.

The jaws 206a and 206b can each include an electrode configured to deliver electricity to tissue (optionally through the grip plates 209a and 209b), and a frame supporting the electrode. The blade slots 224a and 224b of the grip plates 209a and 209b can together be configured to receive a blade between the jaws 206a and 206b, when the jaws are moved out of the open position. In some examples, only one blade slot may be used.

Each of the inner shaft 210 and the outer shaft 208 can be a rigid or semi-rigid and elongate body having a geometric shape of a cylinder, where the shape of the inner shaft 210 matches the shape of the outer shaft 208. In some examples, the inner shaft 210 and the outer shaft 208 can have other shapes such as an oval prism, a rectangular prism, a hexagonal prism, an octagonal prism, or the like. In some examples, the shape of the inner shaft 210 can be different from the shape of the outer shaft 208.

The inner shaft 210 can extend substantially proximally to distally along the axis A1, which can be a longitudinal axis. In some examples, the axis A1 can be a central axis. Similarly, the outer shaft 208 can extend substantially proximally to distally along the axis A1. In some examples, the axis A1 can be a central axis of one or more of the inner shaft 210 and the outer shaft 208. The inner shaft 210 can include an axial bore extending along the axis A1. The outer shaft 208 can also include an axial bore extending along the axis A1. The inner shaft 210 can have an outer dimension (such as an outer diameter) smaller than an inner diameter of the outer shaft 208 such that the inner shaft 210 can be positioned within the outer shaft 208 and such that the inner shaft 210 can be translatable in the outer shaft 208 along the axis A1. The inner shaft 210 can also be referred to as a drive shaft 210, a cam shaft 210, or an inner tube 210. The outer shaft 208 can also be referred to as an outer tube 208.

The blade 212a can be an elongate cutting member at a distal portion of the blade assembly 212. The blade 212a can include one or more sharpened edges configured to cut or resect tissue or other items. The blade assembly 212 can be located within the outer shaft 208 (and can be located within the inner shaft 210). The blade 212a can extend along (and optionally parallel with) the axis A1. The blade 212a can be translatable with respect to the inner shaft 210 and the outer shaft 208 to extend between (or into) the first jaw 206a and the second jaw 206b, such as along the blade slots 224a and 224b. In some examples, the blade 212a can extend axially through the inner shaft 210 offset from the axis A1. In some examples, the blade 212a the blade can extend axially through the flanges 220 and 222 such that the blade 212a is in a position laterally inward of the first set of flanges 220 and the second set of flanges 222. The blade 212a can also be a translating member or electrosurgical component other than a blade. For example, the translating member 212a can be an electrode, such as a blunt electrode, a needle electrode, or a snare electrode.

The guide 218, the drive pin 216, and the pivot pin 214 can each be a rigid or semi-rigid pin, such as a cylindrical pin. The guide 218, the drive pin 216, and the pivot pin 214 can have other shapes in other examples, such as rectangular, square, oval, or the like. In some examples, the pins can all be of the same size but can be different sizes in other examples. Each pin can have a smooth surface to help reduce surface friction between the pins and components of the forceps 200, such as between the pivot pin 214 and the outer shaft 208 or the drive pin 216 and the flanges 220 and 222. Each of the guide 218, the drive pin 216, and the pivot pin 214 can be other components such as one or more projections, bosses, arms, or the like.

In operation, the inner shaft 210 can be translated using an actuator (such as the lever 116 of FIG. 1). The inner shaft 210 can translate with respect to the outer shaft 208 to move the drive pin 216. The drive pin 216 can engage the flanges 220 and 222 to move the flanges 220 and 222 between open and closed positions, which can cause the jaws 206a and 206b to pivot about the pivot pin 214 (such as with respect to the inner shaft 210, the outer shaft 208, or the blade 212) to move the jaws 206 between open and closed positions. Further details and operation of the forceps 200 are discussed below with respect to FIGS. 3A-3C.

Figure 3A:
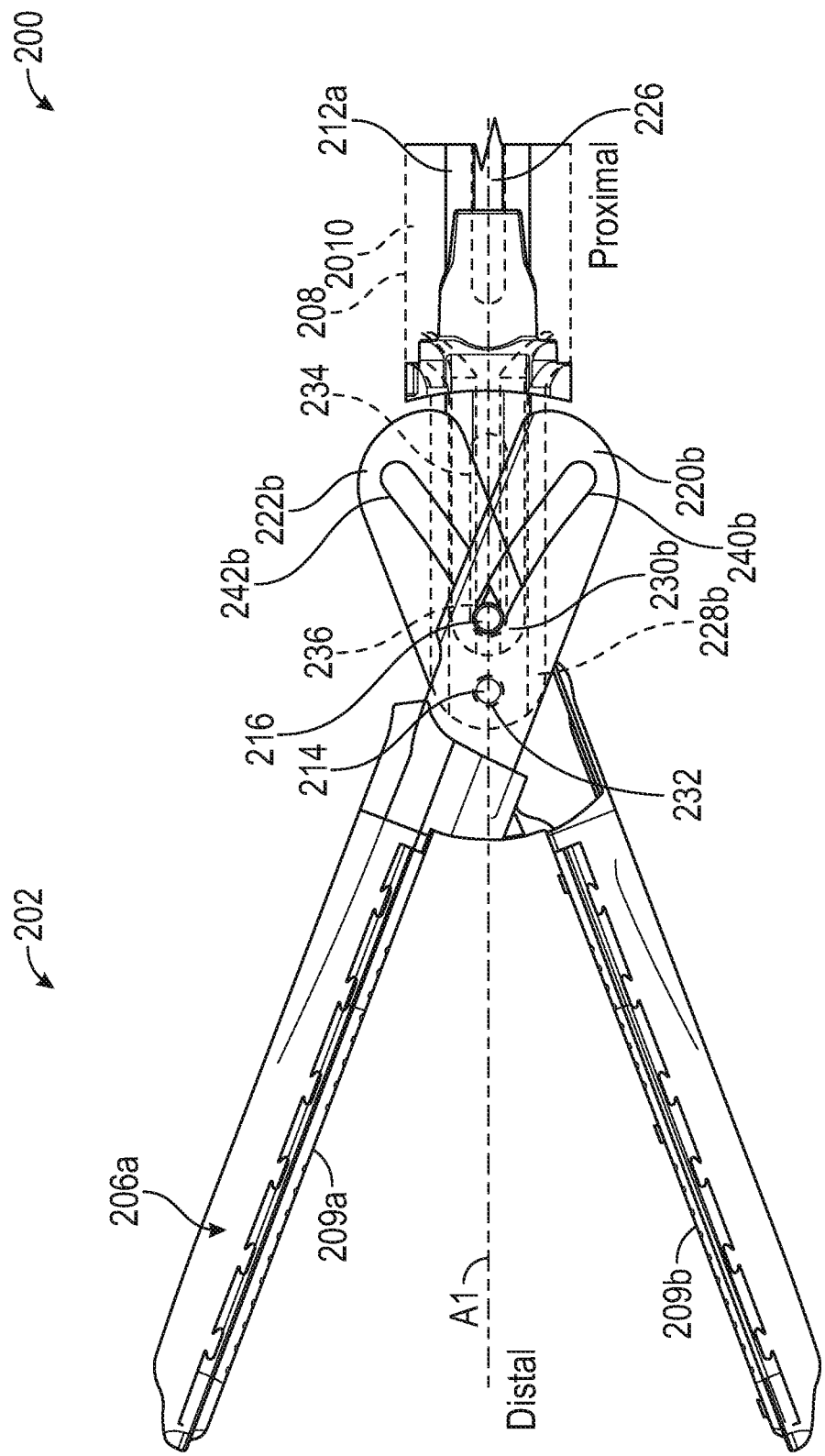
FIG. 3A illustrates a side view of a portion of forceps in an open position.

FIG. 3A illustrates a side view of a portion of forceps 300 in an open position. FIG. 3B illustrates a side cross-sectional view of the forceps 300 in a closed position with a blade 212 retracted. FIG. 3C illustrates a side cross-sectional view of the forceps 300 in a closed position with the blade 212 extended. FIGS. 3A-3C also show orientation indicators Proximal and Distal and are discussed below concurrently.

The forceps 200 of FIGS. 3A-3C can be consistent with the forceps of FIGS. 1A-2C discussed above; FIGS. 3A-3C show additional details of the forceps 200. For example, FIGS. 3A-3C show that the blade 212a can include a blade track 227, which can be a slot, track, guide, or the like extending into or through the blade 212a. The blade track 227 can receive the pivot pin 214 and drive pin 216 therein or therethrough to allow translation of the blade 212a while helping to limit non-translational movement of the blade 212a with respect to the inner shaft 210 and the outer shaft 208. FIGS. 3A-3C also show that the blade 212a can include a sharpened end 226, which can be a sharpened distal edge or portion of the blade 212a. In other examples, other portions of the blade 212a can be sharpened, such as a top or bottom edge of the blade 212a.

FIGS. 3A-3C also show frames 228a and 228b (collectively referred to as frames 228) of the jaws 206a and 206b, respectively. The frames 228 can be rigid or semi-rigid members that can be connected to the flanges 220 and 222 and can be configured to support the grip plates 209 and the housings 230. The housings 230 can be portions of the jaw 206 surrounding the frames 228 and the grip plates 209. The housings 230 can be connected to the flanges 220 and 222. In examples where the jaws 206a or 206b include an electrode, the housings 230 can be made of a plastic or other material that is electrically insulative.

The blade slot 232a can be a slot extending into the housing 230a from the grip plate 209a and can be aligned with the blade slot 224a of the grip plate 209a. Similarly, the blade slot 232b can be a slot extending into the housing 230b from the grip plate 209b and can be aligned with the blade slot 224b of the grip plate 209b. Together, the blade slots 224 and 232 can be configured to receive the blade 212a therein when the blade 212a moves out of the retracted position and into the jaws 206, as shown in FIG. 3C.

The tongue 234a can be a portion of the jaw 206a, where at least a portion of the tongue 234a can be positioned proximal of the grip plate 209a and the tongue 234a can be fixed with respect to the jaw 206a. The tongue 234b can be a portion of the jaw 206b, where at least a portion of the tongue 234b can be positioned proximal of the grip plate 209b and the tongue 234b can be fixed with respect to the jaw 206b. That is, the tongues 234a and 234b do not translate with the inner shaft 210, the outer shaft 208, the drive pin 216, or the blade 212.

The tongues 234a and 234b can be a portion of the housings 230a and 230b, respectively. In some examples, as discussed below, the tongues 234 can be one or more components. Together, the tongues 234a and 234b can be configured to engage tissue between the jaws 206 to help limit proximal movement of the tissue into or between the jaws 206, such as to help prevent tissue from binding the jaws 206 and to help ensure that all desired tissue is sealed (or coagulated) by, for example, electrodes of the jaws 206. Also, the tongues 234a and 234b can be configured to engage tissue to limit proximal extension of tissue beyond a proximal edge of the grip plates 209 (or electrodes).

In some examples, the tongues 234a and 234b can be at least a portion of an overmold of the frames 228a and 228b of the jaws 206a and 206b, respectively. In some examples, the tongues 234a and 234b can be at least a portion of an overmold of a grip plates 209a and 209b of the jaws 206a and 206b, respectively. In some examples, the tongue 234a can be at least a portion of an overmold of the flanges 220 of the jaw 206a and the tongue 234b can be at least a portion of an overmold of the flanges 222 of the jaw 206b. In any of these examples, the grip plates 209a and 209b can be (or can include) an electrode and the overmold can be made of an electrically insulating material, such as one or more of a plastic, ceramic, or the like In operation of some examples, a handle (such as those discussed above) can be operated to translate the inner shaft 210 within (and with respect to) the outer shaft 208. Distal translation of the inner shaft 210 with respect to the outer shaft 208 can cause the drive pin 216 to translate distally causing the jaws 206a and 206b to move from a closed position (as shown in FIGS. 2A, 3B, and 3C) to an intermediate position (as shown in FIG. 2B) to an open position (as shown in FIGS. 2C and 3A). Conversely, proximal translation of the inner shaft 210 can cause the drive pin 216 to translate proximally to move the jaws 206a and 206b to the closed position, such that the drive pin 216 can translate to cause the jaws 206a and 206b to open and close in a scissoring manner. In other examples, the action can be reversed such that distal movement of the inner shaft 210 can cause the jaws 206a and 206b to move toward a closed position and proximal movement of the inner shaft 210 can cause the jaws 206a and 206b toward an open position.

When the jaws 206 are in an open position (as shown in FIG. 3A), the blade 212a can be in the retracted position between the tongues 234a and 234b, proximal of the grip plates 209. When the jaws 206 are in the partially closed position (as shown in FIG. 2B) or when the jaws are not in a fully open position, the blade 212a can be partially extended into the jaws 206a and 206b such as to cut tissue between the jaws 206a and 206b. The blade 212a can be extended by operating the trigger 120 of the handle (or another actuator), as discussed above.

When the jaws 206a and 206b are in the closed position (as shown in FIG. 3C), the blade 212a can be in a retracted position (as shown in FIG. 3B), but can be moved to the extended position (as shown in FIG. 3C). When the blade 212a moves to the extended position, the blade 212a can fully extend into the jaws 206 along the blade slots 224 and 232 such that the blade 212a extends into the housings 230 and the sharpened edge 226 of the blade 212a can cut tissue between the jaws 206. Using these operations, a physician can use the forceps 200 to grasp tissue using the jaws 206a and 206b, resect tissue using the blade 212a, and remove tissue of a patient.

When the blade 212a translates (or reciprocates) from a retracted to an extended position, the blade 212a can be guided to extend into the blade slots 224 and 232 by the tongues 234a and 234b, which can help prevent the edge 226 of the blade 212a from engaging portions of the jaws 206, helping to limit malfunction of the blade 212a during cutting operations. These functions are discussed in further detail below with respect to FIGS. 4A-4C.

Figure 4B:
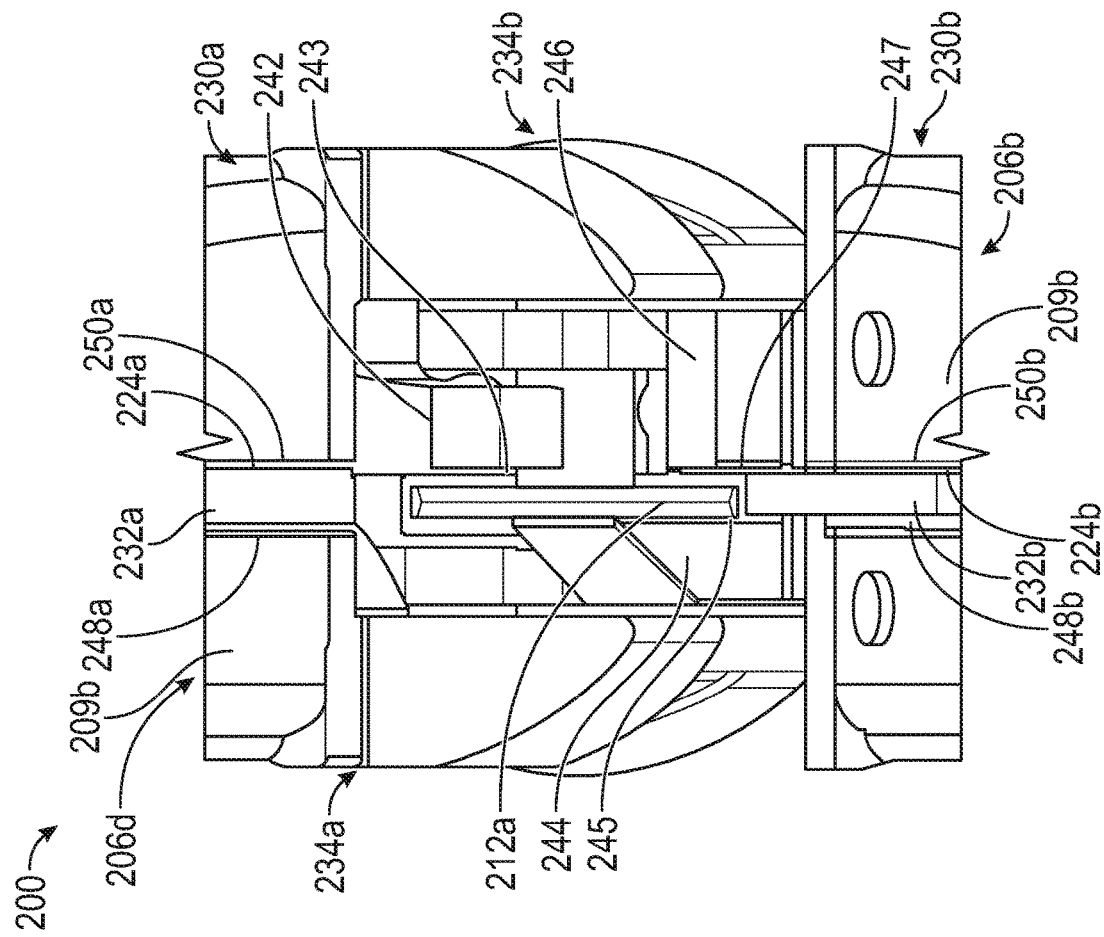
FIG. 4B illustrates a focused end view of a portion of forceps in an open position.
Figure 4A:
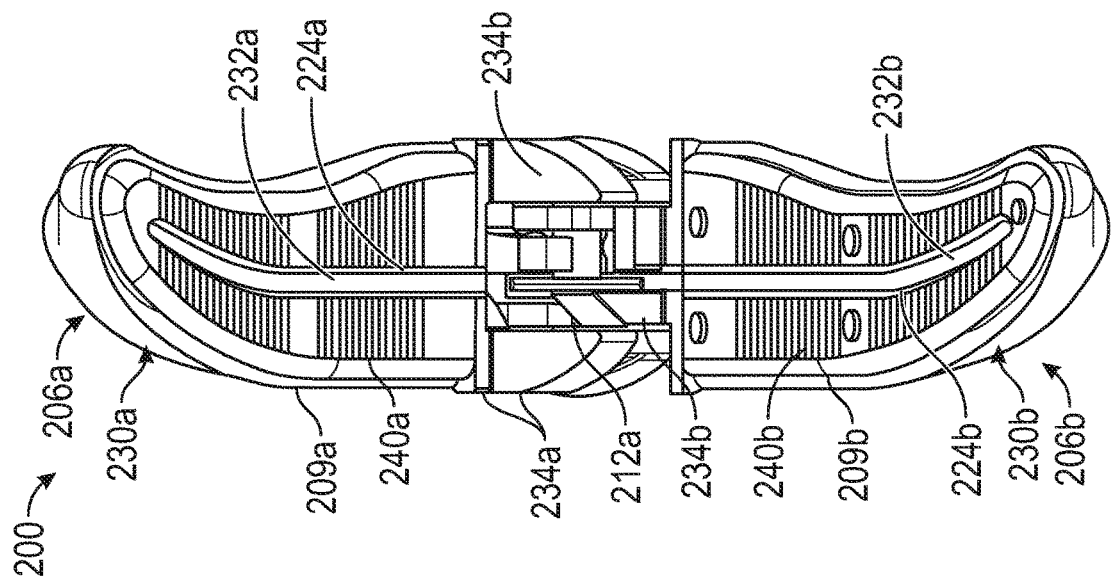
FIG. 4A illustrates an end view of a portion of forceps in an open position.
Figure 4C:
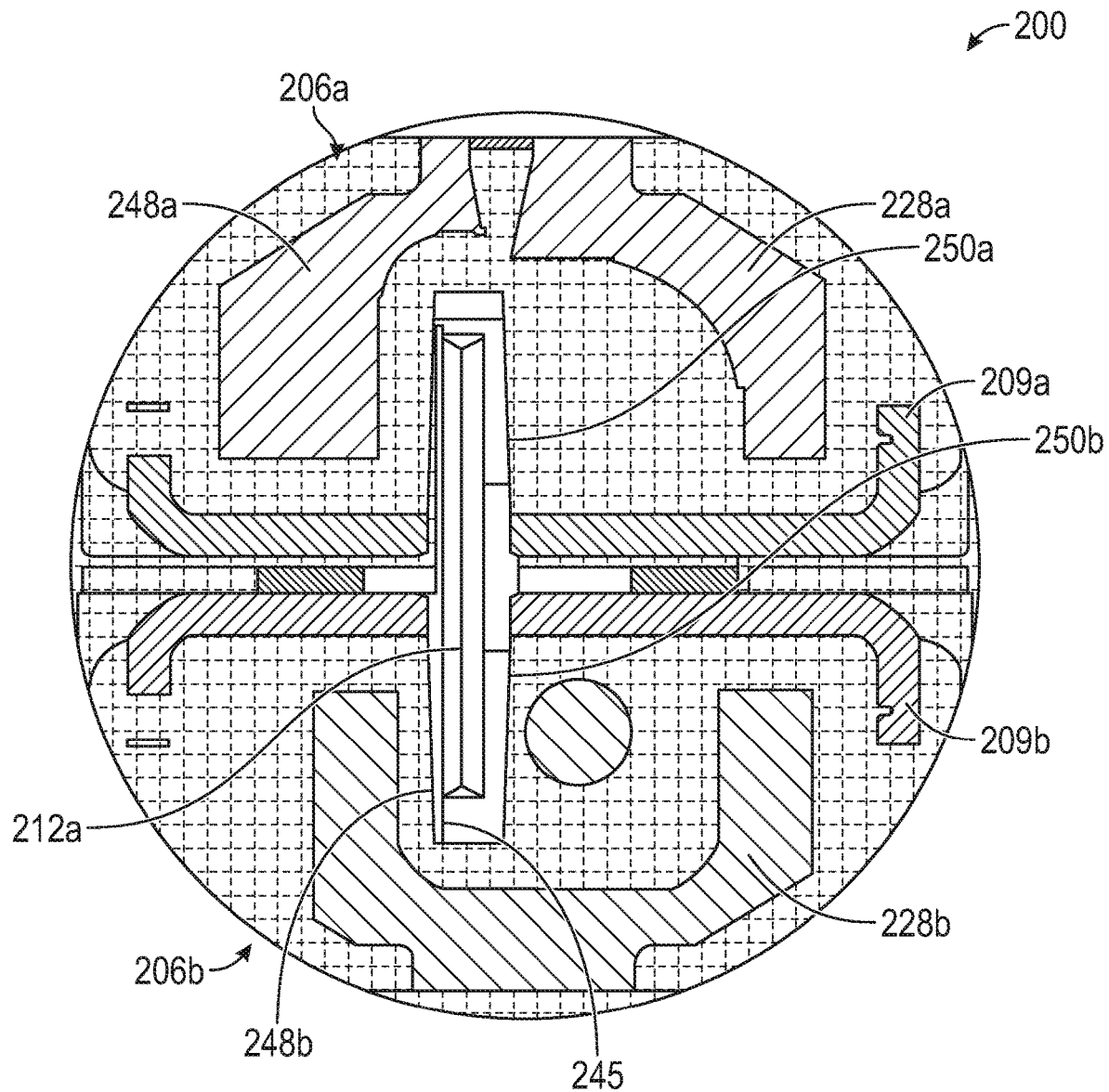
FIG. 4C illustrates a cross-sectional end view of forceps in a closed position across indicators of 4C-4C of FIG. 3B.

FIG. 4A illustrates an end view of a portion of forceps in an open position. FIG. 4B illustrates a focused end view of a portion of forceps in an open position. FIG. 4C illustrates a cross-sectional end view of forceps in a closed position. FIGS. 4A-4C are discussed below concurrently.

The forceps 200 of FIGS. 4A-4C can be consistent with the forceps of FIGS. 1A-3C discussed above; FIGS. 4A-4C show additional details of the forceps 200. For example, FIGS. 4A-4C show that the grip plates 209a and 209b each include a grip surface 240a and 240b (collectively referred to as grip surfaces 240), which can be configured to engage tissue. In examples where the grip plates 209 are electrodes, the one or more portions of the grip surfaces 240 can be configured to deliver energy to tissue in contact with the grip surfaces 240.

The grip surfaces 240a and 240b can help define the blade slots 224a and 224b, respectively. FIGS. 4A-4C show how the blade slots 224a and 224b can be aligned with the blade slot 232a of the housing 230a and the blade slot 232b of the housing 230b, respectively, such that the blade slots 224 and 232 can receive the blade 212a therein. FIGS. 4A-4C also show that the blade slots 224 and 232 can be curved along with the grip plates 209 and housings 230 of the jaws 206. That is, the jaws 206 can be curved with respect to the axis A1.

FIG. 4B also shows that the tongue 234a can include a first tongue 242 including a first wall 243. FIG. 4B also shows that the tongue 234b can include a second tongue 244 including a second wall 245 and the tongue 234b can include a third tongue 246 including a third wall 247.

The first tongue 242 can be a projection or protuberance of the jaw 206a extending toward the jaw 206b. The first wall 243 of the first tongue 242 can be a substantially planar wall and laterally inner surface, but can be other shapes in other examples. The second tongue 244 and the third tongue 246 can be projections or protuberances of the jaw 206b extending toward the jaw 206a. The second wall 245 of the second tongue 244 can be a substantially planar and laterally inner surface, but can be other shapes in other examples. The third wall 247 of the third tongue 246 can be a substantially planar wall and laterally inner surface, but can be other shapes in other examples. Any of the first tongue, 242, the second tongue 244, or the third tongue 246 can be located proximal of the grip plates 209 (which can include one or more electrodes).

FIG. 4B also show that the blade slots 224 and 232 can together define blade slot walls 248 and 250. The slot wall 248 can include a wall 248a of the jaw 206a that can be aligned with a wall 248b of the jaw 206b. Similarly, the slot wall 250 can include a wall 250a of the jaw 206a that can be aligned with a wall 250b of the jaw 206b. The walls 248a and 250a can be substantially parallel walls or surfaces that can at least partially form the blade slots 224a and 232a. Similarly, the walls 248b and 250b can be substantially parallel walls or surfaces that can at least partially form the blade slots 224b and 232b. When the jaws 206a and 206b are moved to a closed position, the walls 248a and 248b can be substantially aligned and the walls 250a and 250b can be substantially aligned to together form the blade slots 224 and 232. The walls 248 and 250 can be spaced with respect to each other to allow for the blade 212a to extend between the walls 248 and 250.

The first wall 243 (or laterally inner surface) of the first tongue 242 can be aligned with (such as laterally aligned with) the walls 250a and 250b. The second wall 245 (or laterally inner surface) of the second tongue 244 can be aligned with (such as laterally aligned with) the walls 248a and 248b. The third wall 247 (or laterally inner surface) of the third tongue 246 can be aligned with (such as laterally aligned with, or coplanar to) the walls 250a and 250b or the first wall 243.

In operation of some examples, the blade 212a can begin in a retracted position between the first tongue 242, the second tongue 244, and the third tongue 246. In such a position, the blade 212a can be located proximally of the grip plates 209. In this position, a distal edge of the blade 212a can be distal to a proximal margin (or proximal end) of the tongues 242, 244, and 246. The edge 226 can be positioned proximally of at least a distal portion all of the tissue stops (such as the tongues 242, 244, and 246), such that the tissue stops help to limit interaction between the blade 212a when the blade 212a is in the retracted position and such that the tissue stops help to limit binding of the jaws 206 caused by tissue extending too far proximally into the jaws 206.

Then, when the blade 212a is translated from the retracted position (as shown in FIGS. 3A and 3B) to the extended position (shown in FIG. 3C), the first wall 243 and the third wall 247 can help to guide the blade 212a into the blade slots 224 and 232 of the jaws 206 by helping to limit contact between the edge 226 of the blade with components of the jaws 206a and 206b. Similarly, the second wall 245 can help to guide the blade 212a, on a laterally opposing side to the first wall 243 and the third wall 247, into the blade slots 224 and 232 of the jaws 206 by helping to limit contact between the edge 226 of the blade with components of the jaws 206a and 206b. Such an action is possible, in part, because the tongues 242, 244, and 246 do not translate with respect to the jaws 206 (or the shafts). Together, the walls of the tongues 242, 244, and 246 can help limit dead-heading of the blade 212a into a component, such prevention can help to limit damage the blade 212a or can help maintain normal operation of the forceps 200.

In some examples, the first wall 243 can be positioned to be nearly aligned with the walls 250, but can be positioned or located laterally outward of the walls 250. Similarly, the third wall 247 can be positioned to be nearly aligned with the walls 250, but can be positioned or located laterally outward of the walls 250. Also, the second wall 245 can be positioned to be nearly aligned with the walls 248, but can be positioned or located laterally outward of the walls 248. Such an arrangement can allow the tongues 242, 244, and 246 to help guide the blade 212a into the blade slots 224 and 232 while helping to reduce interference with the blade 212a proximally of the grip plates 209.

In some examples of this arrangement where the walls 243, 245, and 247 of the tongues 242, 244, and 246, respectively, are positioned laterally outward of the walls 248 and 250, the walls 243 or 247 can be located laterally outward of the wall 250 by a distance less than half a thickness of the blade 212a and the wall 245 can be located laterally outward of the wall 248 by a distance less than half a thickness of the blade 212a.

For example, the blade 212a can have a thickness between 0.25 and 0.26 millimeters (mm) and the distance can be 0.12 millimeters or less. In other examples, the blade 212a can have a thickness between 0.1 and 0.4 millimeters, such as 0.2 millimeters, and the distance can be 0.1 millimeters.

In some examples, the walls 243, 245, and 247 of the tongues 242, 244, and 246, respectively, can be positioned slightly laterally inward of the blade slots 224 and 232, such as when the blade slots 242 and 232 are wider than the blade 212a. For example, FIG. 4C shows that the wall 245 of the second tongue 244 can be positioned slightly laterally inward of the walls 248a and 248b which can be useful where the walls 248 and 250 are not parallel. For example, the walls 248 and 250 can be wider near the grip plates 209 and narrower near laterally or radially outer portions (such as near the frames 228). The narrower portions of the walls 248 and 250 can function to guide the blade 212a while the wider portions near the plates 209 can help to limit contact between the blade 212a and the grip plates 209, which can help limit wear of the blade 212a and the grip plates 209. Also, in examples where the grip plates 209 include an electrode and the blade 212a is electrically charge (hot knife or hot blade), reducing contact between the blade 212a and the grip plates 209 can help limit malfunction of the electrodes or the blade 212. In such an example, the walls 243, 245, or 247 can be aligned with a narrowest portion of the blade slots 232 and 224 to help limit contact between the blade 212a and the grip plates 209. Also, because the tongue 244 can be positioned slightly laterally inward of the walls 248a and 248b, the tongue 244 can help prevent the blade from engaging the a proximal portion of the plate 209 at the corner of the walls 248, which can help limit damage to the blade 212a during operation.

Further, the taper of walls 248 and 250 can be a design feature that can help allow for molding of the overmolded housing (such as the housings 230), such as by reducing use of vertical walls in a direction that the mold opens.

As shown in FIGS. 4A and 4B, the first tongue 242 can be connected to the first jaw 206a and the second tongue 244 and the third tongue 246 can be connected to the second jaw 206b. The tongues 242, 244, and 246 can be connected in other configurations in other examples, as discussed in further detail below.

Figure 5B:
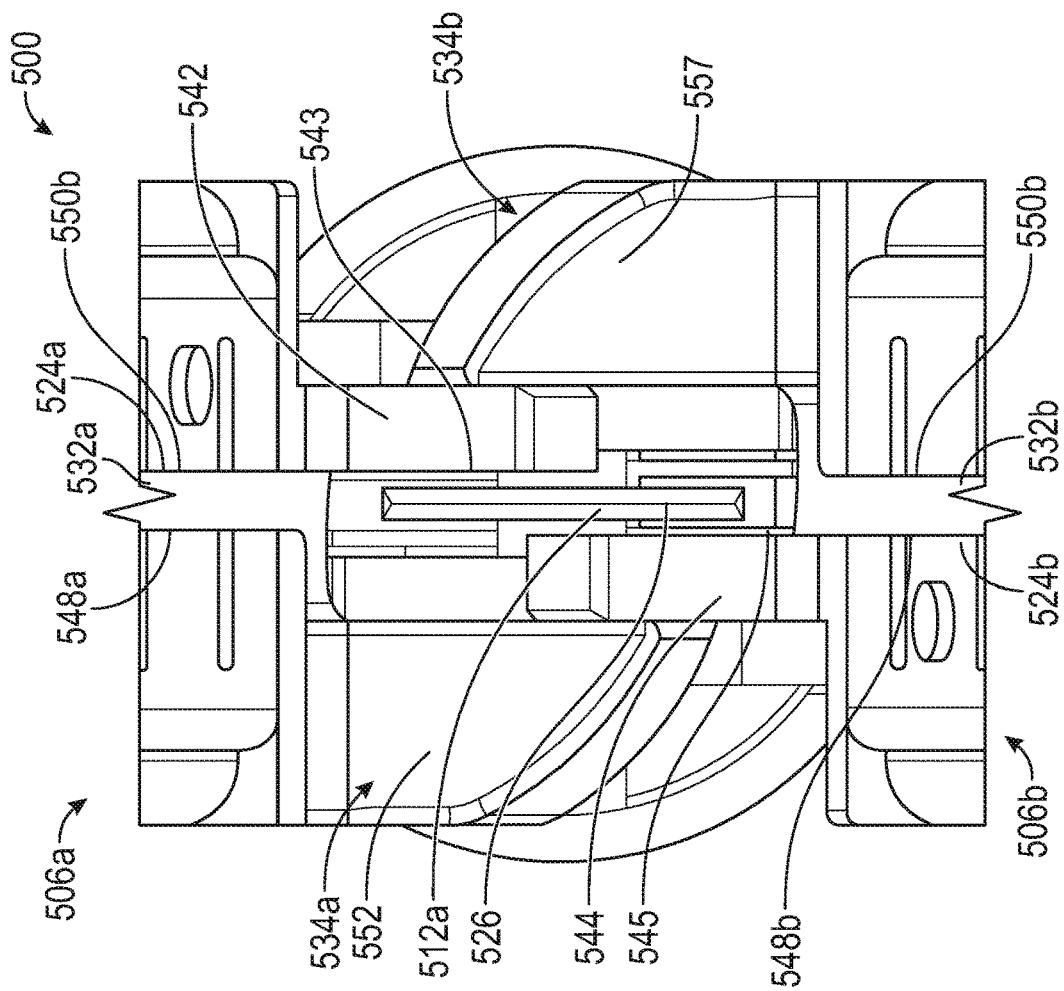
FIG. 5B illustrates a focused end view of a portion of forceps in an open position.
Figure 5A:
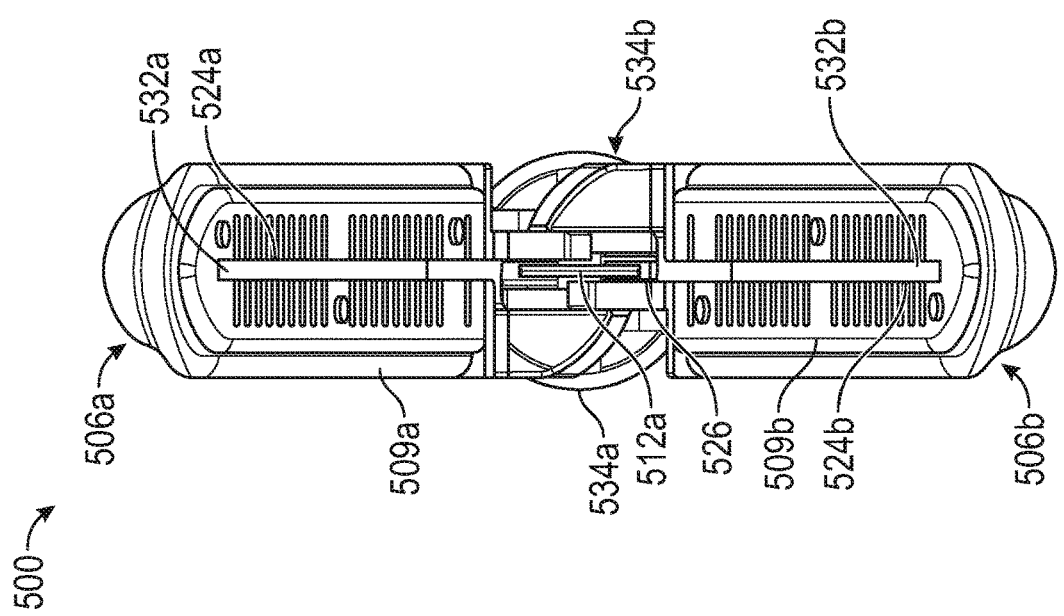
FIG. 5A illustrates an end view of a portion of forceps in an open position.
Figure 5C:
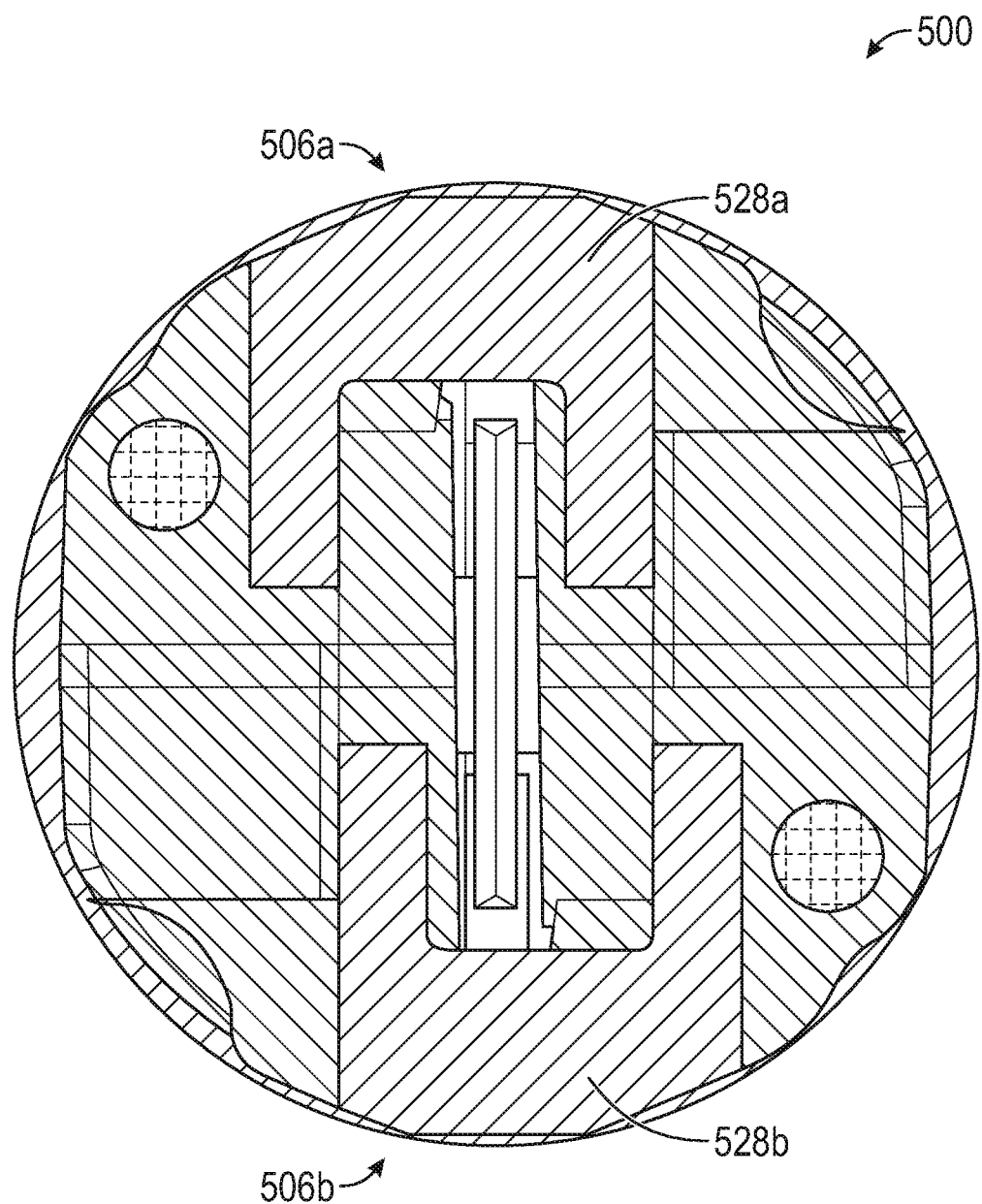
FIG. 5C illustrates a cross-sectional end view of forceps in an open position.

FIG. 5A illustrates an end view of a portion of forceps 500 in an open position. FIG. 5B illustrates a focused end view of a portion of the forceps 500 in an open position. FIG. 5C illustrates a cross-sectional end view of the forceps 500 in an open position. FIGS. 5A-5C are discussed below concurrently.

To forceps 500 can include jaws 506a and 506b (including grip plates 509a and 509b, respectively). The forceps 500 can include a blade 512a including an edge 526. The grip plates 506a and 506b can define blade slots 524a and 524b, respectively. The jaws 206a and 506b can also include frames 528a and 528b which can define blade slots 532a and 532b, respectively. The jaws 206a and 506b can also include tongues 534a and 534b. The tongue 534b can include a first tongue 542 defining a first wall 543 and the tongue 534a can include a second tongue 544 defining a second wall 545. The tongues 534a and 534b can also include tissue stops 552 and 554, respectively.

The forceps 500 can be similar to the forceps 200 discussed above with respect to FIGS. 1-4C except that the jaws 506 can be straight or substantially straight. Because the jaws 506 can be straight, the first jaw 506a can be the same component as the second jaw 506b and when the jaws 506a and 506b are connected, the jaws 506 can be mirror components of each other. FIGS. 5A and 5B show how such an arrangement impacts tongues 534a and 534b of the jaws 506a and 506b, respectively, and how only two tongues 542 and 544 can be used.

FIGS. 5A and 5B show that each jaw 506 can include only a single tongue that is positioned near the blade slots 524 and 532. The first wall 543 of the first tongue 542 can be positioned to be substantially aligned with the walls 550a and 550b. The second wall 545 of the second tongue 544 can be positioned to be substantially aligned with the walls 548a and 548b. Such positioning or location of the tongues 542 and 544 can help to limit contact between the edge 526 of the blade with components of the jaws 506 when the blade 512a is translated from the retracted position (as shown in FIGS. 3A and 3B) to the extended position (shown in FIG. 3C).

Though two tongues are used to help guide the blade 512a into the blade slots 524 and 532 fewer (such as a single tongue) or more (such as 3, 4, 5, 6, 7, 8, or the like) tongues can be used to help guide the blade 512a into the blade slots 524 and 532.

NOTES AND EXAMPLES

The following, non-limiting examples, detail certain aspects of the present subject matter to solve the challenges and provide the benefits discussed herein, among others.

Example 1 is a surgical forceps comprising: a jaw including a grip surface defining a slot; a blade configured to reciprocate along the slot between an extended position and a retracted position; and a tongue connected to the jaw, at least a portion of the tongue proximal of the grip surface to guide the blade into the blade slot when the blade moves from the retracted position into the blade slot.

In Example 2, the subject matter of Example 1 optionally includes a second tongue, at least a portion of the second tongue located proximal of the grip surface to, together with the tongue, guide the blade into the blade slot when the blade moves from the retracted position into the blade slot.

In Example 3, the subject matter of any one or more of Examples 1-2 optionally include a second jaw including a second grip surface.

In Example 4, the subject matter of Example 3 optionally includes wherein the second jaw defines a second slot.

In Example 5, the subject matter of any one or more of Examples 3-4 optionally include wherein the jaw is pivotable with respect to the blade.

In Example 6, the subject matter of any one or more of Examples 3-5 optionally include wherein the second jaw is pivotable with respect to the blade.

In Example 7, the subject matter of any one or more of Examples 3-6 optionally include wherein the jaw and the second jaw are pivotable with respect to the blade.

In Example 8, the subject matter of any one or more of Examples 1-7 optionally include wherein the jaw includes an electrode that at least partially defines the grip surface.

In Example 9, the subject matter of Example 8 optionally includes wherein the tongue is located proximal of the electrode.

In Example 10, the subject matter of any one or more of Examples 1-9 optionally include wherein an inner surface of the tongue is aligned with the blade slot.

In Example 11, the subject matter of any one or more of Examples 1-10 optionally include wherein the tongue includes a first tongue wall aligned with the blade slot, the first tongue wall configured to guide the blade into the blade slot when the blade moves from the retracted position into the blade slot.

In Example 12, the subject matter of any one or more of Examples 1-11 optionally include wherein the jaw includes a second tongue, at least a portion of the second tongue located proximal of the grip surface to, together with the tongue, guide the blade into the blade slot when the blade moves from the retracted position into the blade slot.

In Example 13, the subject matter of Example 12 optionally includes a second jaw including a second grip surface, the second jaw including a third tongue, at least a portion of the third tongue located proximal of the grip surface to, together with the tongue and the second tongue, guide the blade into the blade slot when the blade moves from the retracted position into the blade slot.

In Example 14, the subject matter of any one or more of Examples 1-13 optionally include a second jaw including a second grip surface, the second jaw including a second tongue, at least a portion of the second tongue located proximal of the grip surface to, together with the tongue and the tongue, guide the blade into the blade slot when the blade moves from the retracted position into the blade slot.

In Example 15, the subject matter of any one or more of Examples 1-14 optionally include wherein the tongue is at least a portion of an overmold of a frame of the jaw.

In Example 16, the subject matter of any one or more of Examples 1-15 optionally include wherein the tongue is at least a portion of an overmold of a grip plate of the jaw.

In Example 17, the subject matter of Example 16 optionally includes wherein the grip plate is an electrode and the overmold is electrically insulating.

In Example 18, the subject matter of any one or more of Examples 1-17 optionally include wherein the tongue is at least a portion of an overmold of a first flange of the jaw and a second tongue is at least a portion of an overmold of a second flange of a second jaw.

In Example 19, the subject matter of any one or more of Examples 1-18 optionally include wherein a laterally inner surface of the tongue is aligned with the blade slot.

Example 20 is a surgical forceps comprising: a jaw including a grip plate defining a slot; a blade configured to reciprocate along the slot between an extended position and a retracted position; and a first tongue and a second tongue located proximal of the grip plate, the blade located between the first tongue and the second tongue when the blade is in the retracted position.

In Example 21, the subject matter of Example 20 optionally includes wherein a distal end of the blade is distal to a proximal end of the first tongue and a proximal end of the second tongue.

In Example 22, the subject matter of any one or more of Examples 20-21 optionally include wherein the first tongue and the second tongue are attached to the jaw.

In Example 23, the subject matter of any one or more of Examples 20-22 optionally include a second jaw including a second grip plate.

In Example 24, the subject matter of Example 23 optionally includes wherein the first tongue is connected to the jaw and the second tongue is attached to the second jaw.

In Example 25, the subject matter of any one or more of Examples 23-24 optionally include wherein a position of the first tongue is fixed with respect to the jaw and the second tongue is fixed with respect to the second jaw.

Example 26 is a surgical forceps comprising: a first jaw movably coupled with respect to a second jaw, the first jaw comprising: a grip plate at least partially defining a blade slot; a first jaw housing connected to the grip plate; and a first tongue connected to the first jaw housing and forming a blade guide configured to guide a blade into the first blade slot between the first jaw and the second jaw, the first tongue proximally offset from the first grip plate.

In Example 27, the subject matter of Example 26 optionally includes the second jaw comprising: a second grip plate at least partially defining a second blade slot aligned with the first blade slot and configured to, together with the first blade slot, guide the blade to extend distally between the first jaw and the second jaw.

In Example 28, the subject matter of Example 27 optionally includes the second jaw comprising: a second housing connected to and at least partially surrounding the second grip plate; and a second tongue connected to the second housing and, together with the first tongue, forming the blade guide.

In Example 29, the subject matter of Example 28 optionally includes wherein the first tongue and the second tongue are located on opposing lateral sides of the first blade slot.

In Example 30, the subject matter of any one or more of Examples 28-29 optionally include wherein the first blade slot is at least partially defined by a first slot wall of the first grip plate and a second slot wall of the first grip plate laterally opposing the first slot wall.

In Example 31, the subject matter of Example 30 optionally includes wherein the first tongue includes a first tongue wall and the second tongue includes a second tongue wall, the first tongue wall and the second tongue wall together at least partially defining the blade guide.

In Example 32, the subject matter of Example 31 optionally includes wherein at least a portion of the first tongue wall is laterally aligned with the first slot wall and the second tongue wall is laterally aligned with the second slot wall.

In Example 33, the subject matter of any one or more of Examples 31-32 optionally include wherein at least a portion of the first tongue wall is located laterally outward of the first slot wall by a distance less than half a thickness of the blade.

In Example 34, the subject matter of any one or more of Examples 26-33 optionally include a guide shaft connected to the first jaw and the second jaw, the guide shaft extending along a longitudinal axis and configured to support the blade therein.

In Example 35, the subject matter of any one or more of Examples 26-34 optionally include wherein the first jaw housing is formed as an overmold.

Example 36 is a surgical forceps comprising: a first jaw and a second jaw pivotably coupled with respect to the first jaw, the first jaw comprising: a first grip plate at least partially defining a first blade slot; and a first tongue connected to the grip plate and forming a blade guide configured to guide a blade into the first blade slot, the tongue proximally offset from the first grip plate.

In Example 37, the subject matter of Example 36 optionally includes the second jaw comprising: a second grip plate at least partially defining a second blade slot aligned with the first blade slot configured to, together with the first blade slot, guide the blade to extend distally between the first jaw and the second jaw; a second housing connected to and at least partially surrounding the second grip plate; and a second tongue connected to the second housing and, together with the first tongue, forming the blade guide.

In Example 38, the subject matter of Example 37 optionally includes wherein the first blade slot is at least partially defined by a first slot wall of the first grip plate and a second slot wall of the first grip plate laterally opposing the first slot wall.

In Example 39, the subject matter of Example 38 optionally includes wherein the first tongue includes a first tongue wall and the second tongue includes a second tongue wall, the first tongue wall and the second tongue wall together at least partially defining the blade guide.

In Example 40, the subject matter of Example 39 optionally includes wherein at least a portion of the first tongue wall is laterally aligned with the first slot wall and the second tongue wall is laterally aligned with the second slot wall.

In Example 41, the subject matter of Example 40 optionally includes wherein at least a portion of the first tongue wall is located laterally outward of the first slot wall by a distance less than half a thickness of the blade.

1 In Example 42, the subject matter of any one or more of Examples 36-41 optionally include wherein the blade is limited from extending proximally out of the blade guide.

Example 43 is a surgical forceps comprising: a first jaw comprising: a first grip plate at least partially defining a first blade slot; and a first tongue connected to the grip plate; and a second jaw pivotable with respect to the first jaw, the second jaw comprising: a second grip plate at least partially defining a second blade slot aligned with the first blade slot and configured to, together with the first blade slot, guide the blade to extend distally between the first jaw and the second jaw; and a second tongue connected to the second grip plate and, together with the first tongue, forming a blade guide configured to guide a blade into the first blade slot and the second blade slot, the first tongue and the second tongue configured to engage tissue to limit proximal extension of tissue between the first jaw and the second jaw.

1 In Example 44, the apparatuses or method of any one or any combination of Examples 1-43 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A surgical forceps comprising:
   a jaw including a grip surface defining a blade slot defining a first wall and a second wall opposite the first wall;
   a blade configured to reciprocate along the blade slot between an extended position and a retracted position, the blade including a distal edge;
   a tongue connected to the jaw, at least a portion of the tongue proximal of the grip surface to guide the blade into the blade slot when the blade moves from the retracted position into the blade slot, the tongue defining a first proximal end and a first distal end, and a laterally inner surface of the tongue located laterally inward of the first wall of the blade slot; and
   a second tongue connected to the jaw, at least a portion of the second tongue located proximal of the grip surface to, together with the tongue, guide the blade into the blade slot when the blade moves from the retracted position into the blade slot, the second tongue defining a second proximal end and a second distal end, the distal edge of the blade located distal of the first proximal end and the second proximal end and the distal edge located proximal of the first distal end and the second distal end when the blade is in the retracted position, and a laterally inner surface of the second tongue aligned with the second wall of the blade slot.

2. The surgical forceps of claim 1, wherein the jaw includes an electrode that at least partially defines the grip surface and wherein the tongue is located proximal of the electrode.

3. The surgical forceps of claim 1, wherein the second tongue is located proximal of the grip surface to, together with the tongue, guide the blade into the blade slot when the blade moves from the retracted position into the blade slot.

4. The surgical forceps of claim 3, further comprising:
   a second jaw including a second grip surface, the second jaw including a third tongue, at least a portion of the third tongue located proximal of the grip surface to, together with the tongue and the second tongue, guide the blade into the blade slot when the blade moves from the retracted position into the blade slot.

5. The surgical forceps of claim 4, wherein the distal edge is located distal of a proximal end of the third tongue when the blade is in the retracted position.

6. The surgical forceps of claim 4, wherein the blade is an elongate cutting member.

7. The surgical forceps of claim 4, wherein an inner surface of the third tongue is located laterally inward of the first wall of the blade slot.

8. The surgical forceps of claim 1, further comprising:
   a second jaw including a second grip surface, the second jaw including a third tongue, at least a portion of the third tongue located proximal of the grip surface to, together with the tongue, guide the blade into the blade slot when the blade moves from the retracted position into the blade slot.

9. The surgical forceps of claim 1, wherein the tongue is at least a portion of an overmold of a frame of the jaw.

10. The surgical forceps of claim 1, wherein the tongue is at least a portion of an overmold of a grip plate of the jaw.

11. The surgical forceps of claim 10, wherein the grip plate is an electrode and the overmold is electrically insulating.

12. The surgical forceps of claim 1, wherein the blade is an elongate cutting member.

13. A surgical forceps comprising:
    an outer shaft;
    a pivot pin fixed to the outer shaft;
    a first jaw including a grip plate defining a blade slot, the blade slot defined at least in part by a first wall and a second wall opposite the first wall, the first jaw coupled to the outer shaft by the pivot pin;
    a second jaw including a second grip plate, the second jaw pivotably coupled to the outer shaft by the pivot pin;
    a cam pin located proximal of the pivot pin, the cam pin extending at least partially through the second jaw;
    an inner shaft located at least partially within the outer shaft, the inner shaft movable to move the second jaw between an open position and a closed position;
    a blade located at least partially within the inner shaft, the blade configured to reciprocate along the blade slot between an extended position and a retracted position; and
    a first tongue and a second tongue located proximal of the grip plate, the blade located between the first tongue and the second tongue when the blade is in the retracted position, a laterally inner surface of the first tongue located laterally inward of the first wall, a laterally inner surface of the second tongue aligned with the second wall, and the first tongue and the second tongue engageable with the blade to guide the blade into the blade slot.

14. The surgical forceps of claim 13, wherein a distal end of the blade is distal to a proximal end of the first tongue and a proximal end of the second tongue when the blade is in the retracted position, and wherein the distal end of the blade is proximal to a distal end of the first tongue and a distal end of the second tongue when the blade is in the retracted position.

15. The surgical forceps of claim 13, wherein the first tongue and the second tongue are attached to the first jaw.

16. The surgical forceps of claim 13, wherein a position of the first tongue is fixed with respect to the first jaw and the second tongue is fixed with respect to the second jaw.

* * * * *